United States Patent
Merx et al.

[19]

[11] Patent Number: 6,055,059
[45] Date of Patent: Apr. 25, 2000

[54] SYSTEM AND METHOD FOR MEASURING THE DENSITY OF FIBERS PROJECTING FROM A PLANAR SURFACE

[75] Inventors: Brian Charles Merx; Richard Tolan Brown; Robert Hales Lundgreen, all of Roy; Ronald Frank Hales, Riverdale, all of Utah

[73] Assignee: Iomega Corporation, Roy, Utah

[21] Appl. No.: 09/184,544

[22] Filed: Nov. 2, 1998

[51] Int. Cl.[7] .................................................. G01N 21/84
[52] U.S. Cl. ............................................. 356/430; 250/224
[58] Field of Search .................................. 356/372, 4.08, 356/398, 381, 73.1, 429–431, 238, 239, 420, 394; 250/222.1, 224, 204, 233, 559.27, 559.42, 559.12, 559.47

[56] References Cited

U.S. PATENT DOCUMENTS 3,518,441   6/1970   Selgin ................................. 250/559.27
3,730,633   5/1973   Kennedy ............................. 250/559.27

*Primary Examiner*—Frank G. Font
*Assistant Examiner*—Tu T. Nguyen
*Attorney, Agent, or Firm*—Woodcock Washburn Kurtz Mackiewicz & Norris LLP

[57] ABSTRACT

A system and a method for determining the density in which fibers are disposed along a planar surface employs a source of irradiance and a detector of irradiance in optical communication. A planar surface is positioned slightly below the optical path between the source and the detector. The fibers disposed along the planar surface interrupt the transmission of irradiance between the source and the detector. This interruption causes a decrease in the quantity of irradiance reaching the detector, resulting in a corresponding drop in the detector's output voltage. The density in which fibers are disposed along the planar surface can be determined by comparing the detector's voltage output with a pre-established baseline relating voltage output to fiber density.

41 Claims, 4 Drawing Sheets

SYSTEM AND METHOD FOR MEASURING THE DENSITY OF FIBERS PROJECTING FROM A PLANAR SURFACE

BACKGROUND OF THE INVENTION

Removable disk cartridges for storing digital electronic information typically comprise an outer casing or shell that encloses a magnetic, magnetic-optical, or optical disk upon which information can be stored. The cartridge shell often comprises upper and lower halves that are joined together during the manufacturing process of the cartridge. The disk medium is mounted on a hub that rotates freely within the shell. When the cartridge is inserted into a disk drive, a spindle motor in the drive rotates the disk via a hub disposed in the center of the disk. The cartridge shell is typically equipped with an aperture which provides the read/write heads of the disk drive with access to the disk medium. A shutter or door mechanism is often provided to cover the aperture when the cartridge is not in use, thereby inhibiting dust and other contaminants from entering the cartridge and settling on the medium.

Some contaminants inevitably reach the surface of the disk medium during normal use of the cartridge, despite the presence of the cartridge shell and the shutter mechanism. Such contaminants typically originate in the ambient environment and reach the medium through various openings in the shell, e.g., the access opening for the disk hub. Furthermore, magnetic particles may be generated during the cartridge's manufacturing process, and during read/write operations within the disk drive. The noted contaminants can damage the disk medium and the heads of the disk drive, and can lead to a loss of data.

The problem of disk contamination is typically addressed by placing one or more fabric liners on an inner surface of the cartridge shells. These liners often comprise a mixture of non-woven fibers bonded together by a thermal or an adhesive process. A hydroentangling process such as that described in U.S. Pat. No. 5,311,389 may also be used to bond the fibers. An example of a fabric liner is the "DATAP-ROTECH" liner, manufactured by the Veratec Division of International Paper Co., Walpole, Mass. This particular liner comprises mixture of rayon (80%) and nylon (20%) fibers.

Data-cartridge liners are typically affixed to the upper and lower halves of the cartridge shell, and thus form surfaces that lie directly above and below the surface of the medium. Some type of contact is typically set between the surface of the liner and the disk medium. This contact results in a brushing or wiping motion on the medium's surface as the medium rotates, thereby removing contaminants from the surface.

One method for bringing about contact between the liner and the disk medium is through the use of lifters and opposing ribs. The lifters and ribs are positioned on the inner surface of the cartridge shells, and cooperate in a manner that forces the liner against at least a portion of the medium. This concept is illustrated in U.S. Pat. Nos. 4,750,075; 5,006,948; 5,083,231; and 5,216,566. While the use of lifters and ribs ensures that the liner contacts and wipes the surface of the medium, the force with which the liner is pressed against the medium typically creates a significant amount of drag on the medium during rotation. Higher levels of drag necessitate the use of a relatively strong disk-drive motor to rotate the medium (thereby increasing the cost and size of the disk drive). Additionally, relatively high contact pressure accelerates wear of the medium's surface.

An improved method for cleaning the surface of a data-storage medium has been developed. This methodology is based on the use of raised fibers disposed along the surface of the cartridge liner to wipe the surface of the medium (these surface fibers can be visualized as the "fluff" or "fuzz" which forms on the surface of most fibrous materials). The noted methodology is described in detail in pending U.S. patent application Ser. No. 08/613,880, entitled "Fuzzed Fabric Liner for a Disk Cartridge." The use of raised surface fibers to wipe the medium significantly reduces the contact pressure between the liner and medium, thereby alleviating the disadvantages associated with relatively high contact pressures.

The effectiveness of the above-noted methodology is dependent upon the density in which the raised fibers are distributed along the liner surface. The density of the raised surface fibers is set during the manufacturing process of the liner. Specifically, the liner is "fluffed" by brushing and vacuuming the liner surface in a controlled manner. This process causes the bonded surface fibers to loosen or break, and to extend upward from the surface, thereby forming fluff on the surface of the liner. The amount of fluff disposed along the surface is subsequently checked due to the importance of this parameter to the longevity of the disk medium. Specifically, the density in which the raised fibers are disposed along the liner surface is quantified in relation to some measurable baseline.

The noted fluff check is currently performed by measuring the torque required to rotate the disk medium within a fully-assembled cartridge. This methodology is based on the principle that the fibers in contact with the medium generate a force which opposes the medium's rotation. The magnitude of this force is proportional to the degree of contact between the fibers and the liner, which in turn is proportional the amount of liner fluff present. Hence, the amount of fluff can be determined by comparing the measured rotation torque to a previously-established baseline which relates rotation torque to liner fluff.

The rotation-torque methodology has several significant disadvantages. Specifically, the check can only be performed after the cartridge has been fully assembled. Hence, a check cannot be performed at the liner's point of manufacture if the manufacturing location differs from the cartridge-assembly location. Furthermore, identification of a defective liner will necessitate the disassembly or scrapping of a fully-assembled cartridge. Both of these factors adversely affect production efficiency and cost.

A further disadvantage of the currently-practiced fluff check arises from the fact that the results of the check can be influenced by variables in addition to liner fluff. For example, the torque required to rotate the disk medium is influenced by factors such as friction between the shell of the data-storage cartridge and the disk hub. Such additional variables skew the relationship between liner fluff and rotation torque, thereby reducing the precision of the check. Lower levels of precision in production checks generally necessitate corresponding reductions in rejection thresholds. Hence, the currently-practiced methodology can lead to the rejection of liners which, in reality, possess acceptable fluff characteristics.

Thus, a need exists for an improved system and an improved method for measuring the fluff present on fabric liners used in data-storage cartridges.

SUMMARY OF THE INVENTION

The present invention is directed to a system and a method for measuring the density of fibers projecting from a planar surface. The invention employs a source of irradiance in conjunction with a detector of irradiance. The source and the detector are positioned in a manner that causes the detector to be illuminated by irradiance emitted by the source. A planar surface is placed between the source and the detector, slightly below the path of irradiance. The fibers projecting from the planar surface interrupt the passage of irradiance between the source and the detector. This interruption is proportional to the density of the fibers disposed throughout the illuminated area. The interruption produces a corresponding decrease in the quantity of irradiance incident upon the detector, which in turn reduces the voltage output of the detector. The reduced output level of the detector can be compared with a previously-established baseline relating voltage output to the amount of fluff present in the illuminated area. This comparison will yield a value corresponding to the amount of fluff disposed along the illuminated surface.

The disclosed embodiment comprises a system and a method for checking the fluff on a fabric liner used in a data-storage cartridge. The source of irradiance comprises a laser. The source further comprises a lens that focuses the laser beam into a wide, parallel-line profile. This profile causes the beam to illuminate a relatively wide area on the liner surface, thereby allowing a fluff check to be performed without a need for multiple measurements covering different areas on the liner.

BRIEF DESCRIPTION OF THE DRAWINGS

The foregoing summary, as well as the following detailed description of the preferred embodiment, is better understood when read in conjunction with the appended drawings. For the purpose of illustrating the invention, the drawings show an embodiment that is presently preferred. The invention is not limited, however, to the specific methods and instrumentalities disclosed in the drawings. In the drawings.

DETAILED DESCRIPTION OF PREFERRED EMBODIMENT

The present invention provides a system and a method for measuring the density in which raised fibers are distributed along a planar surface (throughout this specification, these raised surface fibers are referred to as "fluff"). A preferred embodiment of the invention is described in connection with a system and a method for measuring fluff on a liner 10 used in a data-storage cartridge. This embodiment is presented for exemplary purposes only, however. Accordingly, the invention should not be limited to the particular embodiment shown, as the invention may be applied to other types of surfaces.

The amount of fluff on the surface of liner 10 is typically set during manufacture of the liner. In an exemplary manufacturing process, liner 10 is initially cut from a piece of fabric. The cutting process forms liner 10 into a shape corresponding to the surface on which the liner will be mounted within the data-storage cartridge. Liner 10 is then attached to the cartridge using an adhesive material. Alternatively, liner 10 may be temporarily affixed to a storage medium such as waxed paper. A series of brushes are subsequently directed over the surface of liner 10 to straighten and raise the fibers disposed along the liner's surface. Following the brushing process, the surface is vacuumed to further raise the surface fibers, and to remove any fibers that were detached by the brushing process. At some point subsequent to the vacuuming process, the density in which the raised fibers are distributed along the surface of liner 10 is measured to ensure that the fluff lies within an acceptable range of values.

Figure 1:
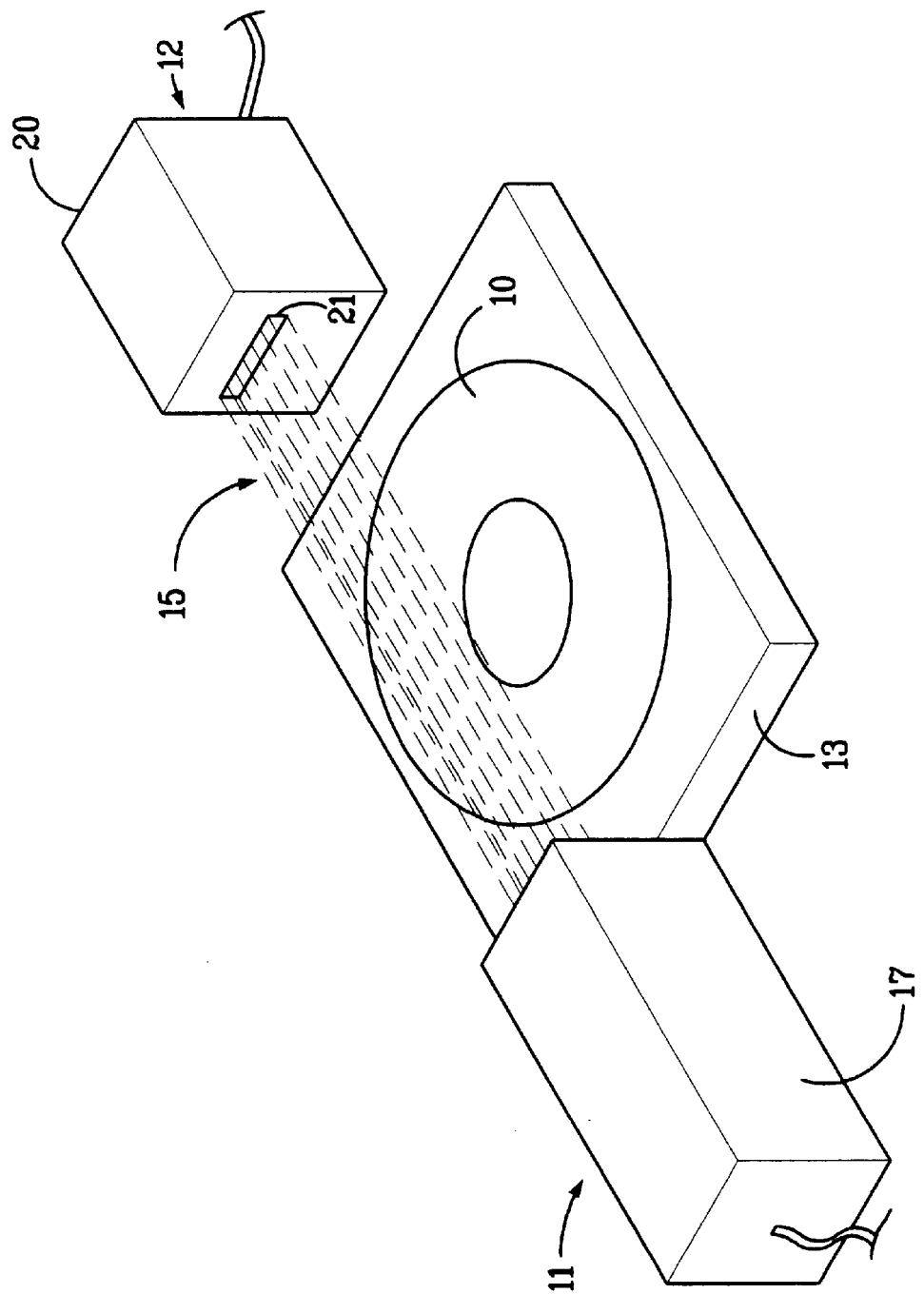
FIG. 1 is an isometric view of a liner fluff measurement system according to the present invention.
Figure 2:
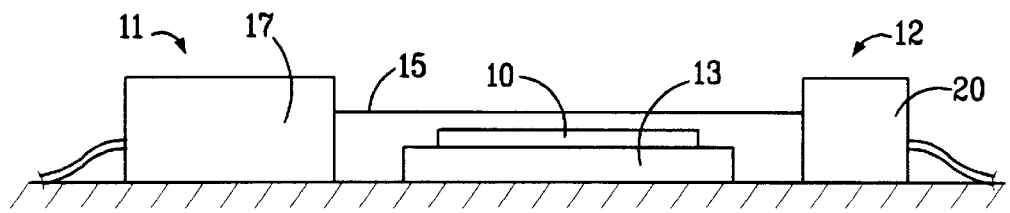
FIG. 2 is a side plan view of the system of FIG. 1.
Figure 3:
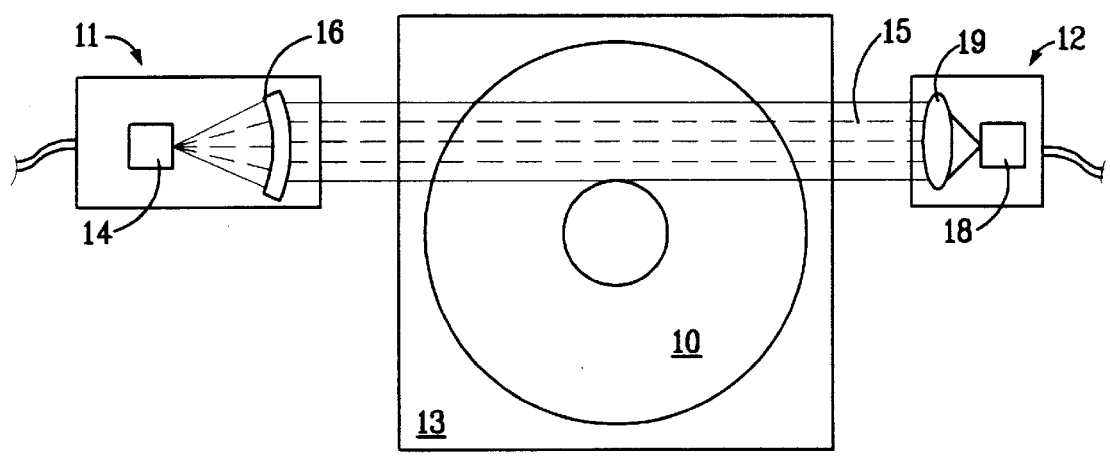
FIG. 3 is a top plan view of the system of FIG. 1.
Figure 4:
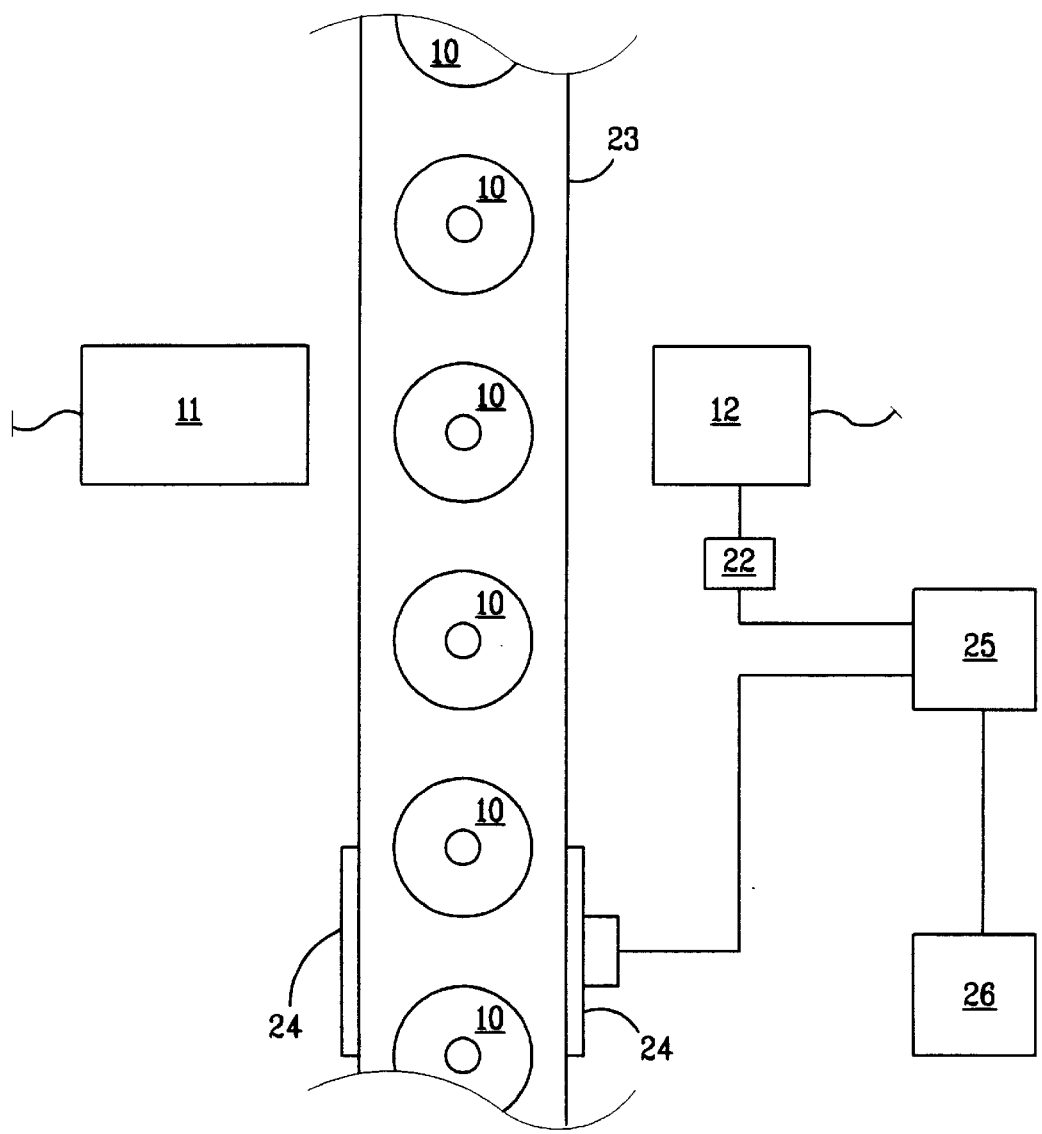
FIG. 4 is a diagrammatic illustration showing the system of FIG. 1 incorporated into an automated system for performing liner fluff checks.

FIG. 1 is an isometric illustration of the invention embodied as a system for measuring liner fluff. FIGS. 2 and 3 are plan views of this embodiment from side and top perspectives, respectively. FIG. 4 is a block diagram showing the embodiment incorporated into an automated system for performing liner fluff checks.

The invention comprises a source of irradiance 11 and a detector of irradiance 12. For illustrative purposes, source 11 and detector 12 are shown in FIG. 3 without any top coverings. Source 11 and detector 12 are positioned in adjacent locations, in a manner that causes source 11 to illuminate detector 12. Preferably, source 11 and detector 12 are separated by about 3.5 inches.

Liner 10 is placed between source 11 and detector 12. Liner 10 is positioned slightly below the optical path between source 11 and detector 12, in such a manner as to cause the irradiance emitted by source 11 to illuminate the fluff on the liner's surface. Liner 10 is shown in the figures as disposed on a raised platform 13. Platform 13 is depicted for illustrative purposes only, as other means may be employed to position liner 10 in the noted manner.

When liner 10 is positioned as described above, the fluff on the liner's surface interrupts the irradiance passing between source 11 and detector 12, thereby reducing the quantity of irradiance reaching detector 12. This reduction is proportional to the amount of fluff projecting from the portion of liner 10 being illuminated by source 11. As explained below, the voltage output of detector 12 will decrease in proportion to the reduction in the amount of irradiance reaching the detector. The reduced output voltage can be compared with a previously-established baseline relating output voltage to liner fluff. Such a comparison will yield a value corresponding to the quantity of fluff projecting from the illuminated area of liner 10.

Source of irradiance 11 preferably comprises a laser 14 that generates a radiant beam 15. Preferably, laser 14 comprises a laser diode. Source 11 further comprises a lens 16 which focuses the output of laser 14 into a parallel-line beam, i.e., a beam that undergoes little or no dispersion after leaving its source. Furthermore, laser 14 and lens 16 preferably generate a "wide beam," i.e., a beam comprising a relatively wide and thin cross-section. Laser 14 and lens 16 are oriented such that the wider dimension of beam 15 lies parallel to the surface of liner 10, as shown in the figures. This orientation allows a relatively large area on liner 10 to be illuminated at one time. Hence, a statistically-significant fluff measurement can be obtained without the need for multiple readings at different locations on liner 10. Preferably, the width of beam 15 is about 0.475 inches. Beam 15 is preferably focused about 25 mils above the surface of liner 10. Source 11 further comprises a housing 17.

Detector 12 comprises a light-receiving element 18, a lens 19, and a housing 20. Irradiance enters detector 12 through an opening 21 in housing 20. Preferably, opening 21 approximates the cross-sectional shape of beam 15, i.e., opening 21 is preferably a slit. Lens 19 subsequently focuses the irradiance onto light-receiving element 18. Detector 12 produces an analog output voltage which is proportional to the quantity of irradiance illuminating light-receiving element 18. As shown in FIG. 4, this output can be directed to an analog-to-digital converter 22 and transformed into a digital value representing the amount of fluff being illuminated by source 11.

A suitable source 11 and detector 12 are available from Keyence Corporation of America, in Woodcliff Lake, N.J., as the LX2 series of laser thrubeam photoelectric sensors.

The present invention can readily be adapted to automated operation. An exemplary embodiment of an automated fluff-check system is illustrated diagrammatically in FIG. 4. This embodiment comprises a plurality of liners 10 disposed on a common strip of material 23, e.g., waxed paper. Strip 23 is grasped by a translating means 24. Translating means 24 moves strip 23 in such a manner as to position an individual liner 10 between source 11 and detector 12 so that a fluff measurement can be acquired. When liner 10 is in position, a microprocessor 25 automatically causes the digitized output of detector 12 to be recorded in a memory device 26. Information identifying the particular liner being evaluated, e.g., the liner's position on strip 23, is also recorded. After the data has been acquired, microprocessor 25 commands translating means 24 to move strip 23 in such a manner as to place another liner 10 into position between source 11 and detector 12.

The present invention possesses a number of advantages over the currently-practiced methodology for checking liner fluff. For example, the invention provides more precise fluff measurements. This improvement arises from the fact that the measurements generated by the invention, unlike rotation-torque measurements, are not affected by extraneous variables unrelated to the amount of fluff present on liner 10. Furthermore, because the fluff check is made before liner 10 is installed in a data-storage cartridge, the invention allows a defective liner 10 to be identified at the time and place of manufacture. Hence, production problems can be identified and corrected in a timely manner, prior to shipment of the liners to a vendee. Finally, a defective liner 10 can be identified before installation in a data-storage cartridge, thereby obviating the need to disassemble or scrap cartridges in which defective liners are later identified.

Figure 5:
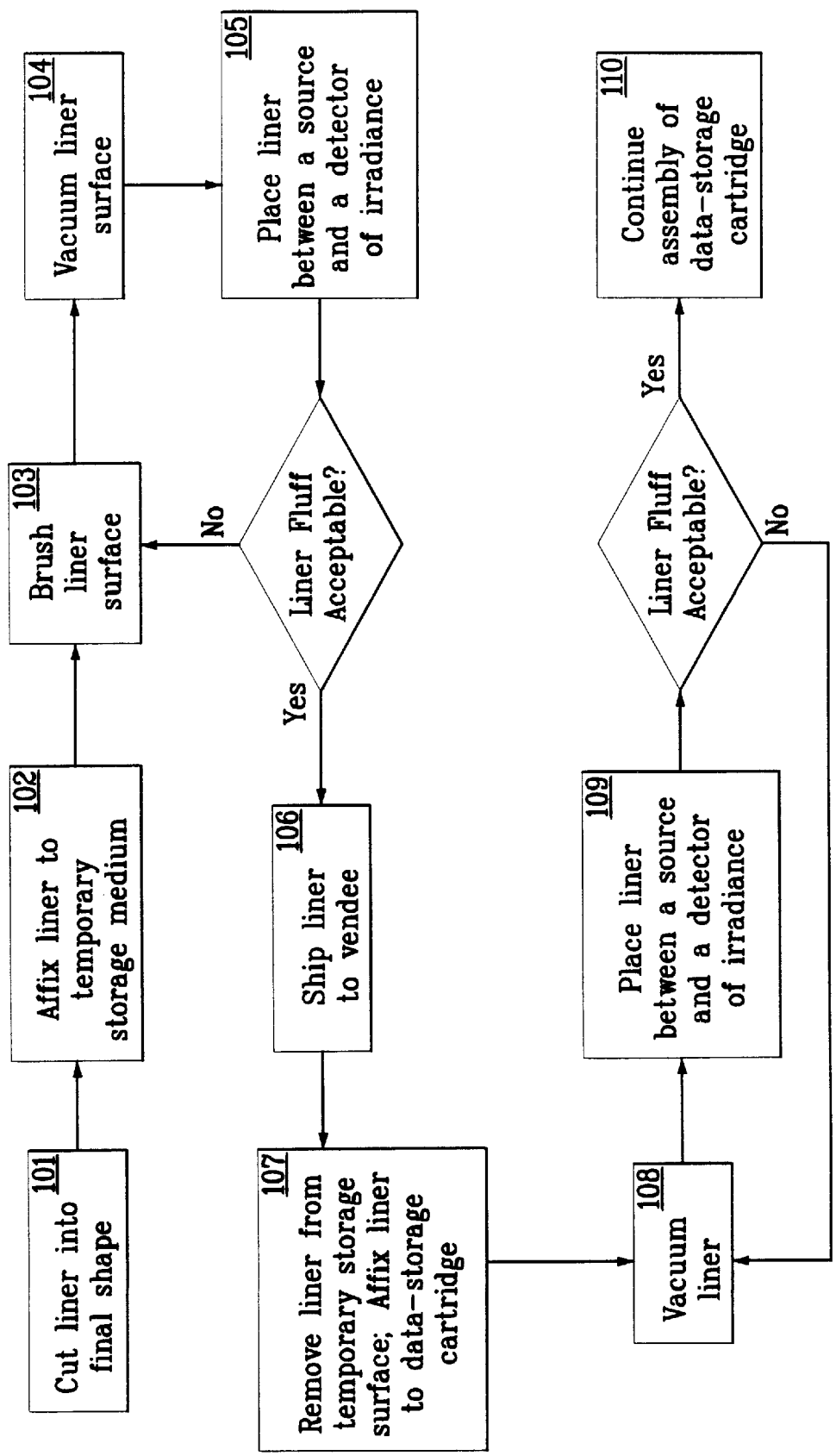
FIG. 5 is a flow chart of a manufacturing process for a data-storage cartridge which incorporates the liner-fluff-measurement methodology of the present invention.

An exemplary liner-manufacturing process made possible by the present invention is illustrated in FIG. 5. As shown in the figure, liner 10 is formed by a cutting process 101 which shapes the liner into its final geometry. Liner 10 is then affixed to a temporary storage medium 102 and fluffed though a process of brushing 103 and vacuuming 104. A fluff check 105 is subsequently performed at the liner's place of manufacture using the present invention. If the fluff check is satisfactory, liner 10 is shipped to a vendee 106, e.g., a manufacturer of data-storage cartridges.

Upon arrival at the cartridge manufacturer, liner 10 is removed from the temporary storage medium and affixed to the shell of a data-storage cartridge 107. Liner 10 is again vacuumed 108 to raise any surface fibers compressed during the affixation process, and a final fluff check 109 is conducted before the shells of the cartridge are joined 110.

The above description of a preferred embodiment is not intended to impliedly limit the scope of protection of the following claims. Thus, except where they are expressly so limited, the claims are not limited to applications involving liners for data-storage cartridges.

What is claimed is:

1. A system for measuring a density of fibers projecting from a planar surface on an object, comprising a source of irradiance, a detector of irradiance which is in optical communication with said source of irradiance, and means for determining a density of said fibers based on an output of said detector, wherein said planar surface is disposed between said source of irradiance and said detector of irradiance so that said irradiance is directed through said fibers in a planar relation to said planar surface, and said fibers inhibit the optical communication between said detector and said source of irradiance.

2. The system of claim 1, wherein said source of irradiance comprises a laser.

3. The system of claim 2, wherein said laser comprises a laser diode.

4. The system of claim 2, wherein said source of irradiance further comprises a lens, said lens being in optical communication with said laser.

5. The system of claim 4, wherein said source of irradiance further comprises a housing for said laser and said lens.

6. The system of claim 4, wherein said lens produces a parallel-line profile in said irradiance.

7. The system of claim 4, wherein said lens produces a wide profile in said irradiance.

8. The system of claim 1, wherein said detector of irradiance comprises a light-receiving element.

9. The system of claim 8, wherein said detector of irradiance further comprises a lens, said lens being in optical communication with said light-receiving element.

10. The system of claim 9, wherein said detector of irradiance further comprises an amplifier, said amplifier being electrically coupled to said light-receiving element.

11. The system of claim 10, wherein said amplifier produces an output voltage, said output voltage being proportional to an amount of said irradiance which is incident upon said light-receiving element.

12. The system of claim 11, wherein said output voltage comprises an analog voltage.

13. The system of claim 12, further comprising an analog-to-digital converter, said converter being electrically coupled to said amplifier.

14. The system of claim 9, wherein said detector of irradiance further comprises a housing, said housing comprising an opening which is in optical communication with said lens.

15. The system of claim 14, wherein said opening comprises a slit.

16. The system of claim 1, wherein said object comprises a liner for a data-storage cartridge.

17. The system of claim 1, further comprising a platform on which said object is disposed.

18. A method for measuring a density of fibers projecting from a planar surface on an object, comprising:
   directing irradiance through said fibers;
   measuring an intensity of said irradiance; and
   comparing said intensity to a baseline intensity to determine said density of fibers.

19. The method of claim 18, wherein said irradiance comprises a laser beam.

20. The method of claim 19, wherein said laser beam comprises a parallel-line profile.

21. The method of claim 19, wherein said laser beam comprises a wide profile.

22. The method of claim 18, wherein said object comprises a liner for a data-storage cartridge.

23. A system for measuring a density of fibers projecting from a liner for a data-storage cartridge, comprising a source of irradiance, a detector of irradiance which is in optical communication with said source of irradiance, and means for determining a density of said fibers based on an output of said detector, wherein said liner is disposed between said source of irradiance and said detector of irradiance so that said irradiance is directed through said fibers in a planar relation to said liner, and said fibers inhibit the optical communication between said detector and said source of irradiance.

24. The system of claim 23, wherein said source of irradiance comprises a laser.

25. The system of claim 24, wherein said laser comprises a laser diode.

26. The system of claim 24, wherein said source of irradiance further comprises a lens, said lens being in optical communication with said laser.

27. The system of claim 26, wherein said lens produces a parallel-line profile in said irradiance.

28. The system of claim 26, wherein said lens produces a wide profile in said irradiance.

29. The system of claim 23, wherein said detector of irradiance comprises a light-receiving element.

30. The system of claim 29, wherein said detector of irradiance further comprises a lens, said lens being in optical communication with said light-receiving element.

31. The system of claim 30, wherein said detector of irradiance further comprises an amplifier, said amplifier being electrically coupled to said light-receiving element.

32. The system of claim 31, wherein said amplifier produces an output voltage, said output voltage being proportional to an amount of said irradiance which is incident upon said light-receiving element.

33. The system of claim 32, wherein said output voltage comprises an analog voltage.

34. The system of claim 33, further comprising an analog-to-digital converter, said converter being electrically coupled to said amplifier.

35. The system of claim 30, wherein said detector of irradiance further comprises a housing, said housing comprising an opening which is in optical communication with said lens.

36. The system of claim 35, wherein said opening comprises a slit.

37. The system of claim 23, further comprising a platform on which said object is disposed.

38. A method for measuring a density of fibers projecting from a liner for a data-storage cartridge, comprising the steps of:

directing irradiance through said fibers;

measuring an intensity of said irradiance; and comparing said intensity to a baseline intensity to determine said density of fibers.

39. The method of claim 38, wherein said irradiance comprises a laser beam.

40. The method of claim 39, wherein said laser beam comprises a parallel-line profile.

41. The method of claim 40, wherein said laser beam comprises a wide profile.

* * * * *